United States Patent [19]

Yanagawa

[11] Patent Number: 5,457,128
[45] Date of Patent: Oct. 10, 1995

[54] TOPICAL PREPARATION FOR HEALING WOUNDS OF THE SKIN

[75] Inventor: Akira Yanagawa, Yokohama, Japan

[73] Assignee: Dott Limited Company, Japan

[21] Appl. No.: 142,468

[22] PCT Filed: Mar. 26, 1993

[86] PCT No.: PCT/JP93/00379

§ 371 Date: Nov. 29, 1993

§ 102(e) Date: Nov. 29, 1993

[87] PCT Pub. No.: WO93/19744

PCT Pub. Date: Oct. 14, 1993

[30] Foreign Application Priority Data

Mar. 28, 1992 [JP] Japan .................... 4-101862

[51] Int. Cl.⁶ .................... A61K 31/045; A61K 9/06
[52] U.S. Cl. .................... 514/532; 514/546
[58] Field of Search .................... 514/532, 546

[56] References Cited

U.S. PATENT DOCUMENTS 4,912,093  3/1990  Michaeli .................... 514/53

OTHER PUBLICATIONS

Daiichi Seiyaku JP 61033116 (Feb. 17, 1986) Derwent Cetraxete topical.
Barsholom WO/PCT89/05646X, 89/05645 (Sep. 29, 1989) Derwent & C.A. 112:84201 Sucralfate–topical.
Baldoni et al. WO/PCT90/02133 (Mar. 8, 1990) Derwent Sucralfate sounds topical/dermal.
Caramella et al. EP 402933 (Dec. 19, 1990) Derwnet Sucralfate Topical.
Peterson et al. WO/PCT9104034 (Apr. 4, 1991) Derwent & C.A. 115:42011 Sucralfate Topical Ulcers/Lesions.
Fabre FR 2646604 (Nov. 9, 1990) CA.114:129165.
Burch et al. Agents Actions 34(1/2)229–231 (1991) CA. 115:174597.
Hayashi et al. J. Pediatr. Sug. 26(11):1279–81 Nov. 1991 Medline Abstrct.
Michaeli EP230023 (Jul. 29, 1987) Derwent & C.A. 108:11249.

Primary Examiner—Shep K. Rose
Attorney, Agent, or Firm—Lorusso & Loud

[57] ABSTRACT

Disclosed is a topical preparation for healing wounds of the skin, which can demonstrate remarkable effects of the treatment of wounds of the skin, such as an ulcer of the skin, traumatogenic wounds caused by the abrasion of the skin, traumatogenic wounds caused by the defect of the skin, an ulcer of the crus, zoster, and so on. The topical preparation contains at least one pharmaceutically effective compound selected from gefarnate, and sofalcone.

5 Claims, No Drawings

TOPICAL PREPARATION FOR HEALING WOUNDS OF THE SKIN

This is a 371 of PCT/JP93/00379 Mar. 26, 1993.

TECHNICAL FIELD

The present invention relates to a topical preparation for healing wounds of the skin, which can demonstrate remarkable effects of the treatment of wounds of the skin, such as an ulcer of the skin, traumatogenic wounds caused by the abrasion of the skin, traumatogenic wounds caused by the defect of the skin, an ulcer of the crus, zoster, and so on.

BACKGROUND ART

As the era of an extraordinarily advanced age is coming in this country, there is a drastically growing increase year by year in the number of the aged who cannot turn their bodies over or a round in bed by themselves. This undoubtedly increases the number of the aged who suffer from wounds of the skin caused by a stayed in bed without turning over or around. Further, there is the increase in numbers of traumatogenic wounds of the skin caused, for example, by traffic accidents. From such background, growing attention has recently been drawn in various fields to the significance of treating skin diseases. In particular, the skin of the aged is in a state considerably different from that of the young in terms of its structure and functions, and there are many different kinds of skin diseases peculiar to the aged. Unfortunately however, currently drugs highly effective for curing or healing such skin diseases has been developed.

Skin diseases occurring in many cases of the aged who cannot turn over or a round in bed by themselves, include intractable skin ulcers such as, for example, decubitus ulcers, burns caused at low temperature, and so on. Further, the aged poor in a systemic state are likely to have their whole bodies infected with opportunistic viruses including herpes viruses such as, for example, simplex virus, cytomegalo virus, or the like. This systemic infection with such viruses may in many cases accompany various symptoms on the skin, like zoster.

On the other hand, currently, as there are no topical preparations suitable for the treatment of skin diseases with a portion of the skin tissues depressed or for the treatment of skin ulcers caused by circulatory disorders such as buerger, diabetes, phlebothrombosis, and so on, such treatment may suffer from difficulty in many cases.

It can be said that a topical preparation capable of applying a medicament directly to the site of lesion is one of the most superior drug delivery systems for administering such a medicament; however, research and studies on such a drug delivery system for administering topical preparations are less advanced. As things stand today, for instance, it can be said that few medicaments have been developed originally for topical application. As topical preparations, there have been extensively employed adrenocortical hormones as if they are an all-round drug therefor. In fact, the adrenocortical hormones are highly effective for many skin diseases; however, careful attention should be paid to the fact that there are many cases in which the application of the adrenocortical hormones worsens a lesion or symptom of some skin disease, e.g. skin ulcers such as decubitus ulcers, burns, etc., zoster and traumatogenic wounds caused by the abrasion of the skin and by the defect of the skin, and so on. Hence, the adrenocortical hormones should not be randomly applied.

In treating the ulcerated skin diseases such as decubitus ulcers, burns at low temperature and crus ulcers as well as the traumatogenic wounds of the skin, the site of a lesion is sterilized and topical preparations containing a chemical agent are applied for the purpose of a prevention of infection. This therapy is dependent mainly upon the natural curing ability of the living body for curing the lesion and symptom of the skin disease. However, as things stand today, few medicaments can positively and actively cure and heal the lesions and symptoms of the skin diseases. In this country, "Bendazac", or [(1-benzyl-1-H-indazol-3-yl)oxy] acetic acid, is the only one that can be adapted to the treatment of ulcers of the skin. Further, bovine blood extract preparations are employed as agents for accelerating the formation of granulation tissues. These medicaments, however, cannot always offer satisfactorily curing effects.

A major therapy for the treatment of the zoster uses topical preparations containing a non-steroid type anti-inflammatory and analgesic agent, while preventing infection with a pathogen by application of an antibiotic ointment. This therapy is conducted mainly in order to mitigate clinical symptoms of the zoster.

It should be noted herein that the term "skin ulcer" or related terms are intended to mean wounds of the skin, caused by the defect of the skin tissues, such wounds having depression to some depth inside the body due to the necrosis of the skin tissues. The term 'skin ulcer' is employed as different from the term "erosion" that is intended to mean wounds of the skin which do not reach the dermis of the skin. The ulcers of the skin may be attributed to various causes. Intractable skin ulcers may include, for example, (1) a decubitus ulcer and a crus ulcer, caused by disorders of local circulation; and (2) skin ulcers caused by burns, frostbite or congelation, disorders by radiation, and so on.

In addition, the zoster caused by infection with cytomegalo virus is such that bullas or blisters occurring in crowds in an initial stage turn gradually into erosion and an ulcer and they are usually cured or healed without particular treatment or naturally in several weeks. In many cases, an ache lasts during this period and such an ache may become less as the exanthema on the skin disappears. However, in order to alleviate pain of a patient, it is of significance to treat and cure the exanthema on the skin.

Furthermore, if a portion of the skin tissues has been lost by an injury or burns or for other reasons, it is needless to say that the skin tissues be repaired immediately to avoid infection. What is common in these disease conditions is the necessity of promoting the propagation of granulation tissues and the sloughing in order to rapidly repair or reflect the skin tissues at the site of the lesion where they are lost due to erosion of the skin, an ulcer or by a physical impact.

In order to improve such defects and disadvantages of conventional medicaments, research has been made for developing new topical preparations for healing wounds of the skin. As a result, there have been made reports on topical preparations containing as a pharmaceutically effective compound (teprenone) (as disclosed in Japanese Patent Examined Publication No. 64-10,495) and (plaunotol) (as disclosed in Japanese Patent Examined Publication No. 2-33,008). However, these topical preparations have not yet entered into the market.

DISCLOSURE OF INVENTION

The present invention has the object to provide a new topical preparation having remarkable properties in enhancing the propagation of the granulation tissue and the formation of a skin crust, or sloughing.

It has been found that at least one compound selected from gefarnate, and sofalcone can exhibit remarkably curing effects upon wounds of the skin. This invention has been completed on the basis of this finding.

The present invention provides a topical preparation for the treatment of wounds of the skin, characterized by containing at least one pharmaceutically effective compound selected from gefarnate, and sofalcone, as an active ingredient. The topical preparation for curing or healing the wounds of the skin (hereinafter sometimes referred to merely as "topical preparation") contains at least one compound selected from four compounds as set forth below, as a pharmaceutically effective ingredient:

(1) Gefarnate (Chemical terminology)
(2) Sofalcone (Chemical terminology) 2'-Carbomethoxy-4,4'-bis(3-methyl-2-butenyl-oxy)chalcone

BEST MODE FOR CARRYING OUT THE INVENTION

The pharmaceutically effective compounds contained in the topical preparations according to the present invention are present in a soluble state in which they are dissolved in an organic liquid or an organic solid, each having compatibility with the pharmaceutically effective compounds to be employed. The pharmaceutically effective compounds may be dissolved in the organic liquid by mixing the pharmaceutically effective compounds with an organic liquid at ambient temperature or at elevated temperature. On the other hand, the pharmaceutically effective compounds may be employed in a liquid form in an organic solid by melting the organic solid by heating and adding the pharmaceutically effective compounds to the heat-molten organic solid. In the topical preparations according to the present invention, it is preferred that the pharmaceutically effective compounds are present in a liquid state or in the form of a solution at ambient temperature.

Gefarnate is not particularly required to be dissolved in such organic liquid because it is in liquid state at ambient temperature; however, as needed, it may be used by dissolving it in an organic liquid showing compatibility therewith. Such organic liquids include, for example, an aliphatic alcohol, a terpene alcohol, a fatty acid ester, an N-alkyl pyrrolidone, an N,N-di-alkyl acetamide, a partial ester of a polyvalent alcohol, an alkylene oxide adduct of a partial ester of a polyvalent alcohol, an alkylene oxide adduct of a mono- or poly-valent alcohol, an alkylene glycol mono-alkyl ether, a di-alkyl imidazolidine, a di-alkyl sulfoxide, and an alkylene carbonate. A non-ionic surface-active agent having an HLB value of 1 to 12 may be employed as such organic liquid.

The aliphatic alcohol may either a mono-valent alcohol or a poly-valent alcohol. Such alcohols may include, for example, a mono-valent alcohol such as ethanol, propanol, isopropanol, octyl alcohol, decyl alcohol, 2-octyl dodecanol, and so on; an alkylene glycol such as ethylene glycol, propylene glycol, butylene glycol, isoprene glycol, and so on; a poly-alkylene glycol such as poly-ethylene glycol, poly-propylene glycol, and so on; as well as glycerin, sorbitol, sorbitan, mannitol, and so on.

As the terpene alcohols, there may be mentioned, for example, farnesol, phytol, patchouli alcohol, and so on.

As the fatty acid esters, there may be mentioned, for example, a mono-valent fatty acid ester such as ethyl myristate, isopropyl myristate, isotridecyl myristate, isopropyl laurate, isopropyl caprylate, isopropyl palmitate, isopropyl butyrate, amyl butyrate, octyl butyrate, and so on; and a di-valent fatty acid ester such as di-ethyl succinate, di-isopropyl succinate, di-ethyl adipate, di-isopropyl adipate, di-isooctyl adipate, di-octyl adipate, di-decyl adipate, decyl-isooctyl adipate, di-ethyl azelate, di-isopropyl azelate, di-isooctyl azelate, di-ethyl sebacate, di-isopropyl sebacate, di-butyl sebacate, di-octyl sebacate, and so on.

The N-alkyl pyrrolidones may include, for example, N-methyl pyrrolidone, N-octyl pyrrolidone, N-dodecyl pyrrolidone, and so on. As the N,N-di-alkyl acetamides, there may be mentioned, for example, N,N-dimethyl acetamide, N,N-di-octyl acetamide, and so on. As the di-alkyl sulfoxides, there may be mentioned, for example, di-methyl sulfoxide, di-octyl sulfoxide, and so on. The alkylene carbonate may include, for example, propylene carbonate, butylene carbonate, and so on.

As the partial esters of the poly-valent alcohols, there may be mentioned, for example, a mono-ester of a higher aliphatic carboxylic acid of the polyvalent alcohol such as mono-stearic acid ester of glycerin, mono-behenic acid ester of glycerin, mono-stearic acid ester of poly-ethylene glycol, mono-stearic acid ester of propylene glycol, mono-stearic acid ester of butylene glycol, mono-oleic acid ester of sorbitan, mono-lauric acid ester of sorbitan, mono-palmitic acid ester of sorbitan, mono-stearic acid ester of sorbitan, mono-isostearic acid ester of sorbitan, and so on.

As the alkylene oxide adduct of the partial ester of the poly-valent alcohol, there may be mentioned, for example, ethylene oxide adduct of mono-stearic acid ester of glycerin, propylene oxide adduct of mono-stearic acid ester of glycerin, ethylene oxide adduct of mono-stearic acid ester of poly-ethylene glycol, propylene oxide adduct of mono-stearic acid ester of poly-ethylene glycol, ethylene oxide adduct of mono-stearic acid ester of propylene glycol, propylene oxide adduct of mono-stearic acid ester of propylene glycol, ethylene oxide adduct of mono-stearic acid ester of poly-propylene glycol, propylene oxide adduct of mono-stearic acid ester of poly-propylene glycol, ethylene oxide adduct of mono-stearic acid ester of butylene glycol, propylene oxide adduct of mono-stearic acid ester of butylene glycol, ethylene oxide adduct or propylene oxide adduct of a mono-fatty acid ester (lauric acid ester, palmitic acid ester, stearic acid ester, oleic acid ester, and so on) of sorbitan, ethylene oxide adduct or propylene oxide adduct of batyl alcohol, and so on.

As the alkylene oxide adducts of the mono- or poly-valent alcohols, there may be mentioned, for example, ethylene oxide adduct or propylene oxide adduct of dodecyl alcohol, ethylene oxide adduct or propylene oxide adduct of glycerin, ethylene oxide adduct or propylene oxide adduct of sorbitan, and so on.

As the alkylene glycol mono-alkyl ether, there may be mentioned, for example, ethylene glycol mono-methyl ether, ethylene glycol mono-ethyl ether, ethylene glycol mono-propyl ether, ethylene glycol mono-octyl ether, isopropylene glycol mono-methyl ether, isobutylene glycol mono-methyl ether, methyl-butylene glycol mono-methyl ether, and so on.

Sucralfate may preferably be dissolved in an organic liquid or be in a soluble state in an organic solid because it is in the solid state at ambient temperature. Such organic liquid may include, for example, an aliphatic carboxylic acid in the liquid state at ambient temperature, such as caproic acid, enanthic acid, caprylic acid, pelargonic acid, linoleic acid, linolenic acid, and arachidonic acid, an N-alkyl pyrrolidone as illustrated above, a di-alkyl sulfoxide as illustrated above, and so on. Such organic solid may include, for example, an aliphatic carboxylic acid in the solid state at ambient temperature, such as lauric acid, myristic acid, palmitic acid, stearic acid, isostearic acid, behenic acid, and so on. Sucralfate may be employed in the form of a solution because it can be dissolved in an acidic aqueous solution or an alkaline aqueous solution.

Cetraxate may preferably be dissolved in an organic liquid or be in a soluble state in an organic solid because it is in the solid state at ambient temperature. Such organic liquid may include those as illustrated above for gefarnate. As such organic solid, there may be mentioned an oily substance existing in the solid state at ambient temperature. Such oily substances may include, for example, a fatty acid ester, an aromatic carboxylic acid ester, a phosphoric acid ester, a higher fatty acid triglyceride, a higher aliphatic alcohol, a higher fatty acid, vaseline, lanolin, bees wax, a solid non-ionic surface active agent, and a mixture thereof.

Sofalcone may preferably be dissolved in an organic liquid or organic solid because it is in the solid state at ambient temperature. As such organic liquid or organic solid, there may be employed those as illustrated above for the cetraxate.

A one mode of the topical preparations according to the present invention contains an oily substance or a surface active agent together with the pharmaceutically effective compound. Such oily substance comprises a substance in the liquid state or in the solid state at ambient temperature and it may include, for example, a fatty acid ester, an aromatic carboxylic acid ester, a phosphoric acid ester, a higher fatty acid triglyceride, a higher aliphatic alcohol, a higher fatty acid, terpene, vaseline, lanolin, liquid paraffin, squalane, bees wax and a mixture thereof.

As the aliphatic fatty acid esters, there may be employed a mono- or poly-valent fatty acid ester, each being in the liquid form or in the solid form at ambient temperature. The fatty acid ester generally comprises a lower or higher alcohol ester having from 1 to approximately 18 carbon atoms of a saturated or unsaturated, straight-chained or branched-chained, mono- or poly-valent fatty acid having from 4 to 22 carbon atoms, preferably from approximately 8 to 18 carbon atoms. As the fatty acid component of the fatty acid ester, there may be mentioned, for example, butyric acid, lactic acid, octanoic acid, isooctanoic acid, dimethyloctanoic acid, nonanoic acid, capric acid, lauric acid, myristic acid, palmitic acid, stearic acid, isostearic acid, oleic acid, behenic acid, adipic acid, azelaic acid, sebacic acid, or the like. On the other hand, the alcohol component thereof, there may be mentioned, for example, ethanol, propanol, isopropanol, butanol, hexanol, decanol, myristyl alcohol, dodecanol, cetyl alcohol, hexadecyl alcohol, behenyl alcohol, or the like. Hence, the preferred examples of the specific fatty acid esters may include, for example, isopropyl myristate, isododecyl myristate, octyl-dodecyl myristate, myristyl myristate, decyl oleate, oleyl oleate, hexyl-decyl iso-stearate, butyl stearate, cetyl isooctanoate, hexyl-decyl di-methyloctanoate, isopropyl palmitate, hexyl laurate, isopropyl caprate, myristyl lactate, oleyl adipate, di-ethyl adipate, di-isobutyl adipate, di-isodecyl adipate, di-octyl adipate, di-benzyl adipate, di-(2-methoxy-ethyl) adipate, di-ethyl sebacate, di-isopropyl sebacate, di-octyl sebacate, di-isopropyl azelate, di-isooctyl azelate, and so on.

As the aromatic carboxylic acid esters, there may be mentioned, for example, di-ethyl phthalate, di-butyl phthalate, di-octyl phthalate, and so on. The phosphoric acid esters may include, for example, tri-oleyl phosphate, tri-decyl phosphate, tri-octyl phosphate, and so on.

Further, the partial esters and the alkylene oxide adducts of the poly-valent alcohols as described hereinabove may be employed as oily substances for the present invention.

The higher fatty acid triglycerides are employed in the liquid form or in the semi-solid form at ambient temperature and a variety of naturally occurring higher fatty acid triglycerides originated from an animal or a plant may be employed. These are generally called fat and oil and they can be extensively available industrially. There may be employed a large number of vegetable oil, beef tallow, liver oil, lanolin, lard, and so on. Preferred are plant oil, in particular olive oil, Tsubaki (camellia) oil, soybean oil, rape-seed oil, corn oil, castor oil, safflower oil, and so on.

As the higher aliphatic alcohols, there may be mentioned, for example, cetanol, stearyl alcohol, behenyl alcohol, lanolin alcohol, farnesol, and so on.

The higher fatty acids may include, for example, octanoic acid, nonanoic acid, capric acid, lauric acid, myristic acid, palmitic acid, stearic acid, oleic acid, linoleic acid, linolenic acid, behenic acid, montanic acid, elaidic acid, and so on.

There may be employed a variety of the surface active agents of the anionic, cationic, non-ionic or amphoteric type and such surface active agents of the non-ionic type are preferred in relation to irritation to the skin. The non-ionic surface active agents may include, for example, surface active agents of an ethylene oxide type, a poly-hydroxy type and a polymer type. As the surface active agents of the ethylene oxide type, there may be mentioned, for example, an ethylene oxide adduct of a higher alcohol, an ethylene oxide adduct of a higher fatty acid, an ethylene oxide adduct of an alkylphenol, an ethylene oxide adduct of an aliphatic amine, an ethylene oxide adduct of an aliphatic amide, an ethylene oxide adduct of a poly-valent alcohol, an ethylene oxide-propylene oxide block copolymer, and so on. The surface active agents of the poly-hydroxy type may include, for example, a mono-fatty acid ester of glycerin, a fatty acid ester of pentaerythritol, a fatty acid ester of sorbitan, a fatty acid ester of sucrose, a fatty acid amide of ethanol amine, and an alkylene oxide adduct thereof. In the present invention, there may advantageously be employed particularly a fatty acid ester of polyoxy-ethylene sorbitan, a mono-fatty acid ester of polyoxy-ethylene glycerin, a mono-fatty acid ester of polyoxy-propylene, a fatty acid ester of sorbitan, polyoxy-ethylene alcohol ether, and so on. These surface active agents may be employed singly or in a mixture thereof.

The topical preparation according to the present invention may contain the pharmaceutically effective compound at the rate ranging from 0.1% to 20% by weight, preferably from 3% to 10% by weight, based on the total weight of the composition. The amount of the oily substance is not restricted to a particular amount and may vary with the desired property of the topical preparation. Further, the amount of the surface active agent is not restricted to a particular amount and it may vary with the desired property of the topical preparation. The surface active agents may generally be used in the amount of from 5% to 50% by weight, preferably from 20% to 45% by weight, based on the total weight of the composition, when the topical preparation is in the form of a non-emulsion type, on the one hand, and from 1% to 20% by weight, preferably from 5% to 15% by weight, based on the total weight of the composition, when the topical preparation is in the form of an emulsion type, on the other hand.

In accordance with the present invention, there may be formulated an alkanol amine as a stabilizer for the pharmaceutically effective compounds. Such alkanol amines may include, for example, di-ethanol amine, tri-ethanol amine, isopropanol amine, di-isopropanol amine, tri-isopropanol amine, di-butanol amine, tri-butanol amine, and so on. The amount of the alkanol amine to be formulated may range from 0.5% to 15% by weight, preferably from 2% to 10% by weight, based on the total weight of the topical preparation.

The topical preparations according to the present invention may contain, as needed, water, a filler, a thickening agent (a polymer), a colorant, a flavoring agent, an emulsion stabilizer, a germicide, a fungicide, and so on. As the filler, finely divided powder of an organic type or an inorganic type may be employed. The particle sizes of the filler may range usually from 0.1 μm to 20 μm, preferably from 0.5 μm to 10 μm. The preferred examples of the fillers may include silica, alumina, titania, resin powder, silicate powder, clay powder, sepiolite powder, montmorillonite powder, fluorine-containing mica powder, hydroxypropyl cellulose powder, and so on.

The topical preparations according to the present invention may be applied in various forms such as ointment, cream, lotion or the like. The compositions of the topical preparations may appropriately be adjusted in order to comply with the forms of the topical preparation products.

When the topical preparations according to the present invention are applied as a mixture in the form of an ointment of a non-emulsion type, the compositions of such topical preparations may preferably comprise the components as follows:

1. Pharmaceutically effective compound:
    0.1%–20% by weight, preferably 3%–10% by weight
2. Organic liquid:
    1%–40% by weight, preferably 2%–20% by weight
3. Oily substance:
    20%–80% by weight, preferably 20%–60% by weight
4. Surface active agent:
    20%–80% by weight, preferably 40%–70% by weight
5. Filler:
    0%–15% by weight, preferably 5%–10% by weight
6. Purified water:
    0%–10% by weight, preferably 1%–5% by weight In the topical preparations comprising the mixture in the ointment form of the non-emulsion type, the oily substance may be employed as an oily substance in the solid form or a mixture comprising an oily substance in the solid form and an oily substance in the liquid form. The topical preparations of this type may contain a surface active agent or agents in the solid form at ambient temperature and/or such oily substance at the amount of from approximately 20% to 80% by weight, preferably from approximately 40% to 70% by weight, based on the total weight of the composition. As the oily substances in the solid form to be employed for such topical preparations, there may be employed the oily substances as described hereinabove. On the other hand, the surface active agents in the solid form may include, for example, a fatty acid ester of a polyoxy-ethylene glycerin such as mono-stearic acid of polyoxy-ethylene (5) glycerin, mono-stearic acid of polyoxy-ethylene (15) glycerin, mono-stearic acid of polyoxy-ethylene (40) glycerin, etc.; a fatty acid ester of a poly-glycerin such as tetra-glyceryl mono-stearate, tetra-glyceryl tris-stearate, deca-glyceryl tri-oleate, etc.; a fatty acid ester of glycerin such as glyceryl mono-palmitate, glyceryl mono-stearate, di-glyceryl di-stearate, etc.; a fatty acid ester of sorbitan such as sorbitan mono-palmitate, sorbitan mono-stearate, sorbitan sesqui-stearate, sorbitan tris-stearate, etc.; a fatty acid ester of a polyoxy-ethylene sorbitan such as polyoxy-ethylene (20) sorbitan tris-stearate, etc.; a fatty acid ester of a polyoxy-ethylene sorbitol such as polyoxy-ethylene (6) sorbitol hexa-stearate, etc.; a fatty acid ester of a poly-ethylene glycol such as poly-ethylene glycol (4 EO) mono-stearate, poly-ethylene glycol di-stearate, etc.; a polyoxy-ethylene-hardened castor oil such as polyoxy-ethylene (80)-hardened castor oil, polyoxy-ethylene (100)-hardened castor oil, etc.; a polyoxy-ethylene-alkyl ether such as polyoxy-ethylene (2)-cetyl ether, polyoxy-ethylene (5)-behenyl ether, etc.; a polyoxy-ethylene-phytosterol such as polyoxy-ethylene (30) phytosterol, etc.; a polyoxy-ethylene-phytostanol such as polyoxy-ethylene (25) phytostanol, etc.; a polyoxy-ethylene-polyoxy-propylene-alkyl ether such as polyoxy-ethylene (20)-polyoxy-propylene (8)-cetyl ether, polyoxy-ethylene (20)-polyoxy-propylene (6)-decyl-tetradecyl ether, etc.; a polyoxy-ethylene-alkylphenyl ether such as polyoxy-ethylene (30)-octylphenyl ether, etc.; a polyoxy-ethylene-lanolin alcohol such as polyoxy-ethylene (40)lanolin alcohol, polyoxy-ethylene (10)-lanolin alcohol, etc.; a polyoxy-ethylene-bees wax derivative such as polyoxy-ethylene (6)-sorbitol bees wax, polyoxy-ethylene (20)-sorbitol bees wax, etc.; and a polyoxy-ethylene-alkyl ether-phosphoric acid such as a di-polyoxy-ethylene (8)-alkyl ether-phosphoric acid, etc. These solid surface active agents may also be employed as the oily substances.

The topical preparations may be prepared by admixing a solution of the pharmaceutically effective compound in the organic liquid with a heat-molten mixture of the surface active agent with the oily substance, adding the filler to the resulting mixture as needed, and then admixing the mixture homogeneously, followed by allowing the resulting mixture to stand to cool.

When the topical preparations according to the present invention are applied as a mixture in the form of an ointment of an emulsion type, the compositions of such topical preparations may preferably comprise the components as follows:

1. Pharmaceutically effective compound:
    0.1%–20% by weight, preferably 3%–10% by weight
2. Organic liquid:
    1%–40% by weight, preferably 2%–20% by weight
3. Oily substance:
    60%–90% by weight, preferably 75%–85% by weight
4. Surface active agent:
    1%–20% by weight, preferably 2%–10% by weight
5. Filler:
    0%–15% by weight, preferably 5%–10% by weight
6. Purified water:
    0%–10% by weight, preferably 1%–5% by weight In the topical preparations as described hereinabove, the oily substances may be employed in the solid form at ambient temperature or as a mixture of an oily substance or substances in the solid form at ambient temperature with an oily substance or substances in the liquid form at ambient temperature. There may be employed the surface active agent having a HLB value of from 8 to 15, preferably from 9 to 12.

The topical preparations of this type may be prepared by gradually adding the pharmaceutically effective compound or a solution A thereof in an organic liquid to a molten mixture B of the oily substance or substances with the surface active agent or agents with stirring at temperature of approximately 60° C. or higher, admixing the resulting mixture with a filler as needed, and allowing the resulting mixture to cool.

When the topical preparations according to the present invention are applied as a mixture in the form of a cream of an emulsion type, the compositions of such topical preparations may preferably comprise the components as follows:
1. Pharmaceutically effective compound:
   0.1%–20% by weight, preferably 3%–10% by weight
2. Organic liquid:
   1%–40% by weight, preferably 2%–20% by weight
3. Oily substance:
   2%–50% by weight, preferably 10%–40% by weight
4. Surface active agent:
   10%–35% by weight, preferably 15%–30% by weight
5. Thickening agent (a water-soluble polymer):
   0.1%–5% by weight, preferably 0.2%–2% by weight
6. Purified water:
   30%–75% by weight, preferably 40%–60% by weight
7. Filler:
   0%–10% by weight, preferably 1%–5% by weight The topical preparations of the type as described hereinabove may be prepared by admixing the pharmaceutically effective compound (1) above with the organic liquid (2) above at elevated temperature to produce a mixture A, admixing the oily substance or substances (3) above with the surface active agent or agents (4) above at elevated temperature to produce a molten mixture B, and adding the mixture A gradually to the molten mixture B with stirring at elevated temperature, followed by adding the thickening agent (5) above and purified water (6) above and, as needed, the filler (7) above and allowing the resulting mixture to cool. The resulting topical preparations may be in the form of an oil/water type emulsion or a water-oil type emulsion. For the topical preparations in the form of the oil/water type emulsion, there may preferably be employed the surface active agent having an HLB value of from 9 to 18. On the other hand, for the topical preparations in the form of the water/oil type emulsion, there may preferably be employed the surface active agent having an HLB value of from 2 to 8. As the oily substance, there may preferably be employed the oily substance in the solid form at ambient temperature or a mixture of the oily substance or substances in the solid form at ambient temperature with the oily substance or substances in the liquid form at ambient temperature. As the thickening agent, there may be mentioned a water-soluble polymer such as a carboxyvinyl polymer, methyl cellulose, hydroxyethyl cellulose, carboxymethyl cellulose, sodium arginate, alginic acid propylene glycol ester, chitosan, polyvinyl alcohol, sodium starch glycolate, and so on.

The topical preparations in the form of such a cream may preferably be prepared by dissolving the pharmaceutically effective compound (1) above in the organic liquid (2) above to yield a solution A, melting a mixture of the solid oily substance or substances (3) above and the solid surface active agent or agents (4) above by heating to yield a molten mixture B, and admixing the resulting mixture with a solution C obtained by dissolving the pharmaceutically effective compound (1) above in the organic liquid (2) above. In the mixing step, attention should be paid to the effect that the temperature of the molten mixture of the oily substance or substances in the solid form at ambient temperature with the surface active agent or agents in the solid form at ambient temperature is held to become higher than the melting points of their components to thereby cause the component or components not to precipitate or deposit as a solid substance or substances.

Then, the mixture prepared above is then fed with the thickening agent (5) above and the purified water (6) above, followed by adding the filler (7) above thereto, as needed, and allowing the resulting mixture to stand to cool. In this step, it is preferred that the thickening agent (5) be added after the addition of the purified water (6); however, the thickening agent (5) may be added together with the purified water (6) by dissolving the former in the latter and adding the resulting solution together with the purified water (6). The purified water (6) may additionally contain other water-soluble substance or substances such as urea, a poly-valent alcohol, and so on. The rate of the urea to be dissolved in advance in the purified water (6) may range from 5% to 20% by weight, preferably from 5% to 10% by weight, based on the total weight of the topical preparation. The purified water (6) may preferably have a pH value ranging from 4.5 to 5.5 and the pH value thereof may preferably be adjusted with a phosphate buffer solution to a desired pH range.

The topical preparations comprising the mixture in the cream form may be prepared by dividing the solution of the pharmaceutically effective compound in the organic liquid into two portions, adding the first portion of the solution to the molten mixture of the oily substance or substances with the surface active agent or agents without stirring or with stirring slowly, and adding the second portion thereof to the resulting mixture with vigorously stirring, thereby mixing all the components homogeneously and yielding the product having remarkable stability in storage.

When the topical preparations according to the present invention are applied in the form of a lotion of a solution type, the compositions of such topical preparations may preferably comprise the components as follows:
1. Pharmaceutically effective compound:
   0.1%–20% by weight, preferably 3%–10% by weight
2. Organic liquid:
   2%–40% by weight, preferably 10%–30% by weight
3. Liquid oily substance:
   0%–30% by weight, preferably 0%–20% by weight
4. Surface active agent:
   0%–20% by weight, preferably 0%–7% by weight
5. Water:
   0%–80% by weight, preferably 0%–60% by weight
6. Thickening agent:
   0.05%–5% by weight, preferably 0.2%–1% by weight The topical preparations in the lotion form may be prepared by dissolving the pharmaceutically effective compound (1) above in the organic liquid (2) above to yield a solution and adding the thickening agent (6) above to the resulting solution, followed by adding thereto the liquid oily substance or substances (3) above, the surface active agent or agents (4) above, and water (5) above, as needed. The resulting topical preparations of the lotion type may be employed as they are as a liquid lotion or as a lotion of an aerosol type by filling the topical preparation in an aerosol can or container together with an aerosol propellant such as liquid natural gases.

The topical preparations according to the present invention may be administered by applying them several times daily, for example, once, twice or three times per day, directly to a site of lesion. They may likewise be applied several times per day in the form of a patch, plaster, poultice or in any other suitable form to a site of lesion. The number of application may appropriately vary depending upon the extent and severity of the disease involved.

The topical preparations according to the present invention can exhibit high effects of treatment, possess a high extent of absorption through the skin and the mucosal membrane and cause no inflammation, because they contain the highly safe pharmaceutically effective compound or compounds that in turn is or are dissolved in the organic liquid or is or are in a soluble state in the organic solid. The topical preparations according to the present invention are administered topically to the site of lesion, not systemically, and they can be administered in highly safe manner without causing any severe side effects such as irritation to the skin, rubor, itching, or the like.

The topical preparations according to the present invention can demonstrate remarkable effects of curing or healing wounds of the skin by the action of the pharmaceutically effective compound or compounds. The wounds thereof may include, for example, an ulcer of the skin such as a decubitus ulcer, burns, and so on; traumatogenic wounds caused by the abrasion or defect of the skin; an ulcer of the crus, derived from diabetes, or any other disease.

When the decubitus ulcer is treated with the topical preparation according to the present invention, the granulation tissues existing at the surface of an ulcer of the skin prior to the treatment, which are in the form of an edema, which are likely to bleed, and which are tinged with white, are replaced with the soft granulation tissues tinged with red. The soft red granulation tissues begin swelling or rising in several days after the treatment. Then, the surface of the ulcer thereof is covered as a whole with the fresh granulation tissues tinged with red in two to four weeks after commencement of the treatment. Thereafter, the sloughing proceeds from the circumferential portion of the ulcer toward its central portion, thereby leading to the healing process in which the surface of the decubitus ulcer becomes smaller and the ulcer is cured.

Further, the topical preparations according to the present invention can offer similar effects in treating ulcers of the skin and wounds thereof caused by burns at low temperature, ulcers of the crus, and zoster. In addition, the topical preparations according to the present invention can demonstrate effects of curing intractable diseases of the skin to an extent remarkably higher than conventional preparations.

EXAMPLES

The present invention will be described more in detail by way of examples.

Example 1

Preparation of Gefarnate Cream A

A mixture comprising 100 grams of gefarnate, 100 grams of olive oil, 30 grams of isopropyl myristate, 30 grams of isotridecyl myristate, 30 grams of behenyl alcohol, 50 grams of whale wax, 30 grams of polyoxyethylene (5)-glyceryl stearate, 30 grams of poly-ethylene glycol mono-stearate and 10 grams of polyoxy-ethylene (2) cetyl ether was dissolved by heating at 82° C. or higher to thereby yield a homogeneous solution (a solution A). Separately, 20 grams of di-isopropanol amine, 30 grams of stearic acid, 50 grams of isoprene glycol, 1 gram of propyl p-aminobenzoate and 1 gram of methyl p-amino-benzoate were added to ca. 450 ml of purified water, and the resulting mixture was warmed to 80° C. to thereby form a homogeneous dispersion (a dispersion B). While the dispersion B was held at 80° C., the solution A was added gradually to the dispersion B with vigorous stirring, thereby forming an emulsion. After completion of the addition of the solution A, the heating was suspended and allowed to cool to 60° to 55° C. Then, while stirring the resulting mixture at room temperature, purified water was added to the mixture cooled to 60° to 55° C. so as to make its total weight to 1 kilogram. The cream product was allowed to stand and bubbles were removed, followed by filling the cream in containers.

Example 2

Preparation of Gefarnate Cream B

A mixture comprising 100 grams of gefarnate, 80 grams of olive oil, 30 grams of isopropyl myristate, 30 grams of isotridecyl myristate, 30 grams of behenyl alcohol, 10 grams of poly-ethylene glycol (molecular weight: 400), 70 grams of cetyl palmitate, 30 grams of polyoxy-ethylene (5)-glyceryl stearate, 20 grams of polyethylene glycol mono-stearate and 20 grams of sorbitan mono-stearate was dissolved by heating at 82° C. or higher to thereby yield a homogeneous solution (a solution A). Separately, 20 grams of di-isopropanol amine, 5 grams of carboxyvinyl polymer, 40 grams of stearic acid, 30 grams of isoprene glycol, 20 grams of butylene glycol, 1 gram of propyl p-aminobenzoate and 1 gram of methyl p-amino-benzoate were added to ca. 463 ml of purified water, and the resulting mixture was warmed to 80° C. to thereby form a homogeneous dispersion (a dispersion B). While the dispersion B was held at 80° C., the solution A was added gradually to the dispersion B with vigorous stirring, thereby forming an emulsion. After completion of the addition of the solution A, the heating was suspended and allowed to cool to 60° to 55° C. Then, while stirring the resulting mixture at room temperature, purified water was added to the mixture cooled to 60° to 55° C. so as to make its total weight to 1 kg. The cream product was allowed to stand and bubbles were removed, followed by filling the cream in containers.

Example 3

Preparation of Sofalcone Cream A

A mixture comprising 100 grams of sofalcone, 60 grams of isopropyl myristate, 50 grams of poly-ethylene glycol 400, 40 grams of cetanol, 60 grams of squalene, 120 grams of polyoxy-ethylene (5)-glyceryl stearate, 20 grams of polyoxy-ethylene (2) cetyl ether and 20 grams of sorbitan mono-stearate was dissolved by heating at 82° C. or higher to thereby yield a homogeneous solution (a solution A). Separately, 20 grams of di-isopropanol amine, 10 grams of carboxyvinyl polymer, 30 grams of propylene glycol, 20 grams of butylene glycol, 1 gram of propyl p-amino-benzoate, 1 gram of methyl p-aminobenzoate and 20 grams of tetracycline hydrochloride were added to 400 ml of purified water, and the resulting mixture was warmed to 80° C. to thereby form a solution (a solution B). While the solution A was held at 82° C., the solution B was added gradually to the solution A with vigorous stirring, thereby forming a water-in-oil emulsion. After completion of the addition of the solution B, the heating was suspended and allowed to cool to 60° to 55° C. Then, while stirring the resulting mixture at room temperature, purified water was added to the mixture cooled to 60° to 55° C. so as to make its total weight to 1 kg. The cream product was allowed to stand and bubbles were removed, followed by filling the cream in containers.

Example 4

Preparation of Sofalcone Cream B

A mixture comprising 100 grams of sofalcone, 10 grams of propylene carbonate, 60 grams of isopropyl myristate, 40 grams of cetanol, 60 grams of squalene, 30 grams of polyoxy-ethylene (5)-glyceryl stearate, 30 grams of poly-ethylene glycol (40 EO) mono-stearate and 20 grams of sorbitan mono-stearate was dissolved by heating at 82° C. or higher to thereby yield a homogeneous solution (a solution A). Separately, 20 grams of di-isopropanol amine, 10 grams of carboxyvinyl polymer, 50 grams of propylene glycol, 1 gram of propyl p-aminobenzoate and 1 gram of methyl p-aminobenzoate were added to 450 ml of purified water, and the resulting mixture was warmed to 80° C. to thereby form a homogeneous solution (a solution B). While the solution B was held at 82° C., the solution A was added gradually to the solution A with vigorous stirring, thereby forming an emulsion. After completion of the addition of the solution A, the heating was suspended and allowed to cool to 60° to 55° C. Then, while stirring the resulting mixture at room temperature, purified water was added to the mixture cooled to 60° to 55° C. so as to make its total weight to 1 kg. The cream product was allowed to stand and bubbles were removed, followed by filling the cream in containers.

Example 5

Preparation of Sofalcone Cream C

A mixture comprising 100 grams of sofalcone, 300 grams of white vaseline, 50 grams of stearyl alcohol, 40 grams of polyoxy-ethylene-hardened castor oil and 10 grams of glycerin mono-stearate was dissolved by heating at 83° C. to thereby yield a homogeneous solution (a solution A). Separately, 120 grams of propylene glycol, 1 gram of propyl p-aminobenzoate and 1 gram of methyl p-aminobenzoate were added to ca. 350 ml of purified water, and the resulting mixture was warmed to thereby form a homogeneous solution (a solution B). While the solution A was held at 80° C. with vigorous stirring, the solution B was added gradually to the solution A, thereby forming a water-in-oil type emulsion. After completion of the addition of the solution B, the heating was suspended and allowed to cool to 60° to 55° C. Then, while stirring the resulting mixture at room temperature, purified water was added to the mixture cooled to 60° to 55° C. so as to make its total weight to 1 kg. The cream product was allowed to stand and bubbles were removed, followed by filling the cream in containers.

Example 6

Preparation of Sucralfate Cream A

A mixture comprising 100 grams of sucralfate, 60 grams of isostearic acid, 30 grams of stearic acid, 80 grams of olive oil, 20 grams of isopropyl myristate, 20 grams of isotridecyl myristate, 30 grams of behenyl alcohol, 30 grams of cetyl palmitate, 30 grams of polyoxy-ethylene (5)-glyceryl stearate, 30 grams of poly-ethylene glycol mono-stearate and 10 grams of polyoxy-ethylene (2) cetyl ether was dissolved by heating at 82° C. or higher to thereby yield a homogeneous solution (a solution A). Separately, 20 grams of di-isopropanol amine, 50 grams of isoprene glycol, 1 gram of propyl p-aminobenzoate and 1 gram of methyl p-aminobenzoate were added to ca. 450 ml of purified water, and the resulting mixture was warmed to 80° C. to thereby form a homogeneous dispersion (a dispersion B). While the dispersion B was held at 80° C., the solution A was added gradually to the dispersion B with vigorous stirring, thereby forming an emulsion. After completion of the addition of the solution A, the heating was suspended and allowed to cool to 60° to 55° C. Then, while stirring the resulting mixture at room temperature, purified water was added to the mixture cooled to 60° to 55° C. so as to make its total weight to 1 kg. The cream product was allowed to stand and bubbles were removed, followed by filling the cream in containers.

Example 7

Preparation of Cetraxate Cream A

A mixture comprising 100 grams of cetraxate hydrochloride, 10 grams of dibutyl adipate, 30 grams of propylene carbonate, 100 grams of olive oil, 30 grams of isopropyl myristate, 30 grams of isotridecyl myristate, 30 grams of behenyl alcohol, 40 grams of cetyl palmitate, 30 grams of stearic acid, 30 grams of polyoxy-ethylene (5)-glyceryl stearate, 30 grams of poly-ethylene glycol mono-stearate and 10 grams of polyoxy-ethylene (2) cetyl ether was dissolved by heating at 82° C. or higher to thereby yield a homogeneous solution (a solution A). Separately, 20 grams of di-isopropanol amine, 50 grams of isoprene glycol, 1 gram of propyl p-aminobenzoate and 1 gram of methyl p-aminobenzoate were added to ca. 450 ml of purified water, and the resulting mixture was warmed to 80° C. to thereby form a homogeneous dispersion (a dispersion B). While the dispersion B was held at 80° C., the solution A was added gradually to the dispersion B with vigorous stirring, thereby forming an emulsion. After completion of the addition of the solution A, the heating was suspended and allowed to cool to 60° to 55° C. Then, while stirring the resulting mixture at room temperature, purified water was added to the mixture cooled to 60° to 55° C. so as to make its total weight to 1 kg. The cream product was allowed to stand and bubbles were removed, followed by filling the cream in containers.

Example 8

A description will be made of effects of the topical preparations according to the present invention when applied clinically.

Case 1

A male patient (67 years of age; complicated with diabetes) with his two arms and two legs paralyzed by the spinal infarction and having a decubitus ulcer as large as ca. 8 cm in longer diameter and ca. 6 cm in a shorter diameter at his sacral portion was treated. He was treated with azulene (Registered Trade Name: Azunol) and a betamethasone valerate ointment (Registered Trade Name: Rinderone VG) for the first two months after hospitalization, then with a bovine erythrocyte extract ointment (Registered Trade Name: Solcoseryl) for the next two months thereafter, and with bendazac ointment (Registered Trade Name: Zildazac) for the additional two months thereafter. However, the therapy with such medicaments did not give improvements whatsoever. After sixth month after hospitalization, therapy with a streptokinase-streptodornase preparation (Registered Trade Name: Validase) and amikacine was tried leading to slight improvement in lesion at the circumferential portion of the decubitus ulcer and the edge portion of the ulcer became slightly clear. Then, therapy with gefarnate cream A prepared in Example 1 above was begun from eleventh month after hospitalization.

In a week after commencement of the application with the gefarnate cream A, the granulation tissues at the site of the ulcer began changing at its peripheral portion from such an edematous form as tinged theretofore with white to a form as tinged with red and the granulation tissues at its peripheral portion began swelling or rising. In two weeks after the therapy with the gefarnate cream A, the sloughing has begun at the peripheral portion of the ulcer and gradually making the ulcer smaller in size and the granulation tissues have risen in the entire area of the ulcer, leading to curing and healing the decubitus ulcer.

Case 2

A male patient at 86 years of age, who kept on lying down due to senile dementia, suffered from a decubitus ulcer having a size as large as ca. 6.5 cm in diameter and reaching the bone at his sacral portion at the time of hospitalization.

The ulcer was treated with gefarnate cream B prepared in Example 2 above. For the first two months after hospitalization, he was treated with infrared therapy and a Zildasac) ointment in vain without any improvements in its lesion, followed by therapy with a bovine erythrocyte extract ointment for the next one month and then by therapy with Povidone iodide (Isodine) sugar for additional two months. The therapy with these medicaments did not give any reaction. Thereafter, his decubitus ulcer was treated intravenously with Validase and washed twice per day with sterilized physiological saline, thereby leading to slight improvement in the lesion at its peripheral portion and making the edge portion of the ulcerated area slightly clear. Then, the therapy with gefarnate cream B was begun and the sloughing at the peripheral portion of the ulcer was recognized to a remarkable extent in a week after the therapy with gefarnate cream B, proliferating the red granulation tissues at the entire surface of the ulcer and having the partially exposed sacral vertebra covered with the fresh granulation tissues to such an extent as invisible from outside. In two weeks, the sloughing occurred to a more apparent extent from the peripheral portion to the central portion of the ulcer, thereby allowing the granulation tissues to rise at the entire surface of the deeply depressed site of the ulcer and leading to curing the decubitus ulcer.

Case 3

A male patient at 64 years of age has undergone a tracheostomy operation because he had failed to recover from conscious and sensorial disorders although he underwent a clipping operation at the time of the subarachnoid bleeding. At the time of hospitalization, he suffered from a decubitus ulcer at his sacral portion, having a size as large as ca. 8 cm in a larger diameter and ca. 6 cm in a shorter diameter, and his ulcer was treated with an (Elen C) ointment and (Isodine) gel for the first one month in vain without producing any improvement. Then, he was administered intravenously with Validase and the lesion of his ulcer was washed with 20 ml of sterilized physiological saline twice per day. In addition, therapy was conducted by application with 200 mg of amikacine for another one month, leading to slight improvements in the lesion and clearing the peripheral portion of the ulcer to some extent. Thereafter, therapy with sofalcone cream A prepared in Example 3 was begun, leading to the proliferation of red granulation tissues at the entire surface of the ulcerated lesion in one week and sloughing from its peripheral portion to its central portion and making the area of the ulcer smaller in two weeks. Then, the granulation tissues were allowed to rise and swell at the entire surface of the ulcerated lesion entering into the curing process.

Case 4

A female patient at 72 years of age, paralyzed partially due to the encephalic bleeding, has suffered from a decubitus ulcer at her sacral portion and treated by application with sofalcone cream C prepared in Example 5. At the time of hospitalization, she had the decubitus ulcer of an irregular shape, having a size as large as ca. 6.5 cm in a larger diameter and ca. 5 cm in a shorter diameter. For the first 20 weeks after hospitalization, she was treated with a Solcoseryl ointment in vain without any improvements in lesion. Then, she was treated with Isodine sugar for the next two months, with an Elen C ointment in addition to therapy with Isodine sugar for another 30 weeks, and then by intravenous administration of Validase together with the washing twice daily with physiological saline for additional two months. The therapy with these medicaments did not cure her decubitus ulcer. Thereafter, she was treated with sofalcone cream C, leading to the proliferation of red granulation tissues from its peripheral portion of the lesion in one week after therapy with sofalcone cream C and sloughing from its peripheral portion toward its central portion to a remarkably increased extent and, at the same time, allowing fresh granulation tissues to grow at its central portion of her ulcerated lesion.

Case 5

A male patient at 65 years of age has suffered from a decubitus ulcer having a size as large as 11 cm by 10 cm at his sacral portion, with its central portion depressed deeply inside by ca. 1.5 cm to 2 cm and with his sacral periosteum exposed to outside. He was treated with 3–5 grams of sofalcone cream A twice per day, leading to the formation of granulation tissues toward its central portion from its peripheral portion in a spiral form at its entire edge portion in one week after therapy with sofalcone cream A. Further, the granulation tissues are allowed to arise or swell to such an extent as reaching the height of the skin surrounding the ulcerated lesion. The exposed area of the sacral periosteum was covered with fresh granulation tissues in two weeks, thereby offering remarkable improvements in lesion.

Case 6

A male patient at 76 years of age has suffered from a decubitus ulcer having a size as large as 6.8 cm by 9.5 cm at his sacral portion, with its central portion depressed deeply inside by ca. 1.5 cm to 2 cm and with his sacral periosteum exposed to outside. He was treated with 3–5 grams of sucralfate cream A prepared in Example 6 twice per day, leading to the formation of granulation tissues toward its central portion from its peripheral portion in a spiral form at its entire edge portion in one week after therapy with the sucralfate cream A. Further, the granulation tissues are allowed to arise or swell to such an extent as reaching the height of the skin surrounding the ulcerated lesion. The exposed area of the sacral periosteum was covered with fresh granulation tissues in two weeks, thereby offering remarkable improvements in lesion.

Case 7

A male patient at 83 years of age has suffered from a decubitus ulcer having a size as large as 2.5 cm by 3.5 cm at his sacral portion, with its central portion depressed deeply inside by ca. 1.5 cm to 2 cm and with his sacral periosteum exposed to outside. He was treated with 3–5 grams of cetraxate cream A prepared in Example 7 twice per day, leading to the formation of granulation tissues toward its central portion from its peripheral portion in a spiral form at its entire edge portion in one week after therapy with the cetraxate cream A. Further, the granulation tissues are allowed to arise or swell to such an extent as reaching the height of the skin surrounding the ulcerated lesion. The exposed area of the sacral periosteum was covered with fresh granulation tissues in two weeks, thereby offering remarkable improvements in lesion.

Case 8

Three cases of crus ulcers caused by various background factors (Buerger, a female patient at 49 years of age; diabetes, two male patients at 55 years of age and at 64 years of age, respectively) were treated with gefarnate cream A prepared in Example 1. These crus ulcers have been treated with various therapy at least for one year and they gave no response at all to such therapy. However, in one week after therapy with the gefarnate cream A, the granulation tissues at the surface of the ulcerated lesion began rising or swelling by replacing the tissues in the edema form tinged theretofore with white by the tissues tinged with red. The sloughing has begun from its edge portion in two to four weeks, reducing the size of the ulcerated lesion and raising the granulation tissues at the entire surface of the ulcer and leading to curing.

Case 9

A male patient (76 years old), who has kept lying on bed, suffered from an intractable ulcer caused by burns, and he was treated with gefarnate cream A prepared in Example 1 above. This therapy gave highly cured effects.

Case 10

A male patient at 25 years of age suffering from traumatogenic wounds derived from the abrasion of the skin caused by traffic accident and a male patient at 41 years of age suffering from traumatogenic wounds derived from the defect of the skin caused by an accident during work were treated with sofalcone cream B. In each case, the therapy with the sofalcone cream B led to the proliferation of fresh granulation tissues and to the formation of crusts in the area of the lesion in several days after commencement of such therapy. The course of the lesion has proceeded well thereafter.

It is further confirmed that the topical preparations according to the present invention can demonstrate remarkable effects of curing the ulceration of the skin derived from angiitis caused by malignant articular rheumatism, the ulceration of the skin derived from the occlusive endarteritis caused by scleroderma, in addition to the wounds of the skins as described hereinabove.

I claim:

1. A topical preparation for the treatment of wounds of the skin containing at least one pharmaceutically effective compound selected from gefarnate and sofalcone, as an active ingredient, and a pharmaceutically acceptable carrier.

2. A topical preparation for the treatment of wounds of the skin containing at least one pharmaceutically effective compound selected from gefarnate and sofalcone, an organic liquid, a solid oily substance, and a surface active agent.

3. A topical preparation as claimed in claim 2, wherein said topical preparation is a mixture in the form of an ointment containing said solid oily substance in an amount of from 20% to 80% by weight based on the total weight of said topical preparation.

4. A topical preparation as claimed in claim 2, wherein said topical preparation is a mixture in the form of a cream containing water and a thickening agent.

5. A topical preparation for healing wounds of the skin, comprising a solution of at least one pharmaceutically effective compound selected from gefarnate and sofalcone in an organic solvent liquid.

* * * * *

UNITED STATES PATENT AND TRADEMARK OFFICE
CERTIFICATE OF CORRECTION

PATENT NO. : 5,457,128
DATED : October 10, 1995
INVENTOR(S) : Akira YANAGAWA

It is certified that error appears in the above-indentified patent and that said Letters Patent is hereby corrected as shown below:

Col. 1, line 19, "a round" should read --around--;
    line 22, "stayed" should read --stay--;
    line 30, after "tunately" insert a comma --,-- and after "currently" insert --few--;
    line 32, delete "the";
    line 33, "a round" should read --around--;
    line 65, delete "the", second instance.

Col. 3, line 52, after "may" insert --be--.

Col. 10, line 8, delete "rate" insert --amount--.

Signed and Sealed this

Twentieth Day of August, 1996

Attest:

BRUCE LEHMAN

Attesting Officer    Commissioner of Patents and Trademarks